United States Patent
Buckland et al.

(10) Patent No.: US 10,172,977 B2
(45) Date of Patent: *Jan. 8, 2019

(54) POROUS BIOMATERIAL

(71) Applicant: ApaTech Limited, Elstree, Hertfordshire (GB)

(72) Inventors: Thomas Buckland, Aylesbury (GB); Charles Campion, Barnet (GB)

(73) Assignee: APATECH LIMITED, Elstree, Hertfordshire (GB)

(*) Notice: Subject to any disclaimer, the term of this patent is extended or adjusted under 35 U.S.C. 154(b) by 103 days.

This patent is subject to a terminal disclaimer.

(21) Appl. No.: 15/236,093

(22) Filed: Aug. 12, 2016

(65) Prior Publication Data

US 2016/0346434 A1 Dec. 1, 2016

Related U.S. Application Data

(63) Continuation of application No. 12/865,633, filed as application No. PCT/GB2009/000296 on Feb. 2, 2009, now Pat. No. 9,533,075.

(30) Foreign Application Priority Data

Feb. 1, 2008 (GB) .................................. 0801935.8

(51) Int. Cl.
A61L 27/56 (2006.01)
A61L 27/12 (2006.01)
A61L 27/02 (2006.01)
A61F 2/28 (2006.01)

(52) U.S. Cl.
CPC ............. *A61L 27/56* (2013.01); *A61L 27/025* (2013.01); *A61L 27/12* (2013.01); *A61F 2/28* (2013.01); *A61L 2400/08* (2013.01); *A61L 2430/02* (2013.01); *Y10T 428/2982* (2015.01)

(58) Field of Classification Search
CPC ............ C12Q 1/6827; C12Q 2565/125; C12Q 2565/501; A61F 2/28; A61L 2400/08; A61L 2430/02; A61L 27/025; A61L 27/12; A61L 27/56; Y10T 428/2982
See application file for complete search history.

(56) References Cited

U.S. PATENT DOCUMENTS

| | | | |
|---|---|---|---|
| 6,210,412 B1 | 4/2001 | Michelson | |
| 6,302,913 B1 | 10/2001 | Ripamonti et al. | |
| 6,511,510 B1 | 1/2003 | de Bruijn et al. | |
| 2001/0032022 A1* | 10/2001 | Ricci .................. | A61F 2/30767 623/23.56 |
| 2002/0165616 A1 | 11/2002 | Heide et al. | |
| 2004/0078087 A1 | 4/2004 | Kim et al. | |
| 2006/0110422 A1 | 5/2006 | Tas et al. | |
| 2007/0218098 A1 | 9/2007 | Reif et al. | |

FOREIGN PATENT DOCUMENTS

| | | |
|---|---|---|
| DE | 29922585 U1 | 7/2000 |
| EP | 1449818 A1 | 8/2004 |
| EP | 1584338 A2 | 10/2005 |
| EP | 0951441 B1 | 7/2006 |
| EP | 1829564 A1 | 9/2007 |
| GB | 2142919 A | 1/1985 |
| WO | WO9628117 A1 | 9/1996 |
| WO | WO0020353 A1 | 4/2000 |
| WO | WO0042991 A1 | 7/2000 |
| WO | WO0062829 A1 | 10/2000 |
| WO | WO2006082442 A1 | 8/2006 |
| WO | WO2006115398 A1 | 11/2006 |
| WO | WO2007094672 A1 | 8/2007 |
| WO | WO2007124511 A2 | 11/2007 |

OTHER PUBLICATIONS

Ferraz et al., Effect of chemical composition on hydrophobicity and zeta potential of plasma sprayed HA/CaO-P2O5 glass coatings, Biomaterials (2001), 22(23)3105-3112.

Habibovic et al., 3D microenvironment as essential element for osteoinduction by biomaterials, Biomaterials (2005), 26(17)3565-3575.

Habibovic et al., Relevance of osteoinductive biomaterials in critical-sized orthotopic defect, J Orthop Res (2006), 24 (5):867-876.

Klucakova, Analysis of relationship between properties and behaviour of materials used and impregnation conditions of carbon—carbon composites, Acta Materialia (2005), 53(14)3841-3848.

Kwon et al., Synthesis and dissolution behavior of β-TCP and HA/β-TCP composite powders, Journal of the European Ceramic Society (2003), 23(7):1039-1045.

Lopes et al., Hydrophobicity, surface tension, and zeta potential measurements of glass-reinforced hydroxyapatite composites, J Biomed Mater Res (1999), 45(4)370-375.

Yamasaki et al., Osteogenic response to porous hydroxyapatite ceramics under the skin of dogs, Biomaterials (1992), 13(5):308-312.

Liu, Fabrication of hydroxyapatite ceramic with controlled porosity, Journal of Materials Science: Materials in Medicine (1997), 8(4):227-232.

(Continued)

Primary Examiner — Ernst V Arnold
(74) Attorney, Agent, or Firm — K&L Gates LLP

(57) ABSTRACT

A synthetic osteoinductive porous biomaterial is provided comprising: a network of interconnected micropores, wherein the microporosity is 23% by volume or more; wherein the surface free energy of the biomaterial is 19 mJ/m or more; and the mean interconnection diameter and the mean interconnection diameter and the surface free energy are chosen to provide a permeability resulting from the micropores of 0.206 nm2 or greater and a capillary pressure difference in water of 3.7 kPa or more. The biomaterial contains hydroxyapatite and silicon.

10 Claims, No Drawings

(56) References Cited

OTHER PUBLICATIONS

GB Search Report dated May 29, 2008, issued in related application No. GB0801935.8, 2 pages.
GB Search Report dated Jun. 25, 2009, in related application No. GB0800335.2, 1 page.
U.S. Office Action dated May 17, 2012, issued in related U.S. Appl. No. 12/865,573.
U.S. Office Action dated Dec. 26, 2012, issued in related U.S. Appl. No. 12/865,573 (15 pages).

* cited by examiner

POROUS BIOMATERIAL

The present invention relates to an osteoinductive biomaterial. More particularly, the present invention relates to a biomaterial having a defined pore structure and specific physical properties that promote osteoinductive properties in the material.

BACKGROUND TO THE INVENTION

When a bone-replacement material is implanted in patient, the formation of living bone may be induced at the surface of the bone. This is termed osteoconduction. In addition, living bone may in certain circumstances form within the material itself, penetrating the structure of the bone-replacement material. This is termed osteoinduction.

When osteoinduction occurs, bone is formed at a non-bony (i.e. ectopic) site. Osteoinduction is thought to be beneficial because, over time, the growth of bone penetrating a material can result in the more resilient integration of the bone-replacement material into already existing bone at, for example, the site of an osseous defect. However, many osteoconductive biomaterials do not exhibit osteoinduction.

Osteoinduction is promoted and/or accelerated by osteoinductive materials. In other words, osteoinductive materials are capable of inducing bone growth and the formation of bone in non-osseous tissue. When implanted in patients, osteoinductive materials are of significant therapeutic value because they promote and accelerate bone growth. For example in patients with compromised bone biology, the promotion and acceleration of bone repair can lead to shorter fracture-repair times and a lower incidence of non-unions or pseudo-arthroses.

To date, the most popular way of achieving osteoinduction in a biomaterial has been to include powerful cytokine proteins in a therapeutic form. The best known and most widely used of these proteins are the Bone Morphogenetic Proteins (BMP), particularly BMP-2 and BMP-7. These have been provided as recombinant human proteins (as present for example in the 'InFuse'® and 'OP-1' bone replacement materials currently on the market), or as gels, powders or fibres derived from highly processed cadaver human bone and generically referred to as Demineralised Bone Matrix (DBM).

The disadvantages of using these proteins are well-known. While Bone Morphogenetic Protein products are certainly effective in their ability to promote rapid bone growth in preclinical studies, the use of recombinant human Bone Morphogenetic Protein products can also result in significant negative side-effects, such as uncontrolled bone resorption, runaway bone formation and, from a financial viewpoint, extremely high costs per therapeutic unit. Numerous clinical adverse events have been recorded using these highly-potent therapies, some resulting in major harm to patients. The mechanisms behind the occurrence of these adverse events are not currently well-understood.

In addition, the performance of products derived from Demineralised Bone Matrix is known to be highly variable and very donor-dependant. One solution to this would be to batch mix products from different donors. However, as all Demineralised Bone Matrix products have to maintain lot traceability, batch mixing is not possible. In addition, the levels of Bone Morphogenetic Proteins (from which the Demineralised Bone Matrix's osteoinductive properties are thought to derive) are very low and below established therapeutic thresholds for predictable, repeatable performance. As a result of these drawbacks, Demineralised Bone Matrix products have not demonstrated equivalent performance to current, commonly-used therapies in other equivalent orthopaedic and neurosurgical fields.

Another disadvantage of conventional Bone Morphogenetic Protein products is that they are not localised to a persistent scaffold which supports bone growth. Specifically, Bone Morphogenetic Protein products are typically provided as liquids which have to be adsorbed onto suboptimal scaffolds. The unpredictability of the absorption process can result in insufficient adsorption of the proteins, followed by implant compression and extrusion of the active agent into nerve spaces, causing severe harm or disability once bone formation has eventually been induced.

An alternative approach to relying on intentionally-introduced Bone Morphogenetic Proteins to provide osteoinductive activity is to provide a material having intrinsic osteoinductivity. The material is typically a scaffold material that itself promotes and accelerates bone growth without having to be treated with Bone Morphogenetic Proteins before being implanted into a patient.

One approach to provide an osteoinductive material has been to select a material that is resorbable. For example, the dissolution of calcium and phosphate from a calcium phosphate material are thought by some to be the key to providing an osteoinductive material. This approach is extended in, for example, PCT/NL2006/000210, which suggests that the dissolution of certain trace elements from a calcium phosphate material further promotes osteoinduction.

Another example of material that is claimed to have intrinsic osteoinductivity is described in U.S. Pat. No. 6,302,913. This material is "bioinert", but, according to U.S. Pat. No. 6,302,913, has a surface geometry with a series of concavities that is said to concentrate Bone Morphogenetic Proteins absorbed from circulatory fluid in order to induce bone formation. However, these types of materials have also not yet resulted in strong in vivo promotion of bone growth.

As a result of at least some of the drawbacks with the prior art, the inventors of the present invention have set about to provide a material having intrinsic osteoinductivity but without relying on the sometimes unpredictable dissolution of trace elements or manipulation of surface geometry to provide osteoinduction.

EP 0951441 describes the synthesis of a dense osteoconductive silicon-substituted hydroxyapatite material.

SUMMARY OF THE INVENTION

The present invention provides a synthetic osteoinductive porous biomaterial comprising: a network of interconnected micropores, wherein the microporosity is 23% by volume or more; wherein the surface free energy of the biomaterial is 19 mJ/m$^2$ or more, and the mean interconnection diameter and the surface free energy are chosen to provide a permeability resulting from the micropores of 0.206 nm$^2$ or greater and a capillary pressure difference in water of 3.7 kPa or more.

The present invention further provides a synthetic osteoinductive porous biomaterial comprising: a network of interconnected micropores, wherein the microporosity is 23% by volume or more; wherein the surface free energy of the biomaterial is 20 mJ/m$^2$ or more, and the mean interconnection diameter is 0.5 to 2.0 µm.

The present invention further provides a synthetic porous biomaterial as defined herein for use in medicine. The present invention also provides a method of treating bone fractures, achieving spinal fusions, repairing bone tumours or vertebral compression fractures, the method comprising implanting a biomaterial as defined herein in a patient or animal.

The present invention further provides method of selecting a porous osteoinductive biomaterial and providing osteoinduction of the bone, the method comprising: (a) selecting an osteoinductive porous biomaterial having the following characteristics: (i) a network of interconnected micropores having a microporosity set to 17.5% by volume or more; (ii) a surface free energy set to 19 mJ/m$^2$ or more, (iii) a permeability resulting from the micropores set at 0.206 nm$^2$ or greater, and (iv) a capillary pressure difference in water set to 3.7 kPa or more; and (b) configuring said osteoinductive biomaterial as a replacement bone-material for osteoinduction.

DETAILED DESCRIPTION OF THE INVENTION

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The inventors have recognised the advantage for patients of providing an osteoinductive biomaterial over a purely osteoconductive biomaterial.

Some known scaffold materials rely on the dissolution of the scaffold to provide osteoinductivity and, as a result, must be resorbable under biological conditions in order to provide osteoinduction.

The inventors have surprisingly found that porous biomaterials can be provided that have an action of bone growth that is directly associated with the actual biomaterial itself, rather than bone growth being promoted by the biomaterial's surface geometry or resorption properties. In particular, the inventors have found that a combination of specific structural and surface properties of the biomaterial impart osteoinductivity on the biomaterial itself. Unlike other ways of providing osteoinductivity, the present invention's osteoinductivity is relatively independent of the chemical composition of the biomaterial, although certain materials do have preferred osteoinductive properties.

In particular, the inventors have found that, in order to render it osteoinductive, a porous biomaterial beneficially exhibits a combination of properties. Firstly, the inventors have found that the porous body beneficially has a sufficiently high number of pores having a small interconnect diameter so that the biomaterial possesses a high capillary action to adsorb liquids from biological fluid. This results in a high concentration of the bone growth-promoting proteins naturally present in the biological fluid in a confined environment. The inventors have also found that the porous body beneficially provides a surface environment that is conducive to the attachment and absorption of bone-growth promoting proteins and facilitates the capillary action of the porous body.

Accordingly, the biomaterial of the present invention may be described as an osteoinductive biomaterial.

The control of the number of pores having a small interconnect diameter and the control of surface environment results in the control of a combination of permeability, absorption capacity into the body, adsorption capacity onto the surface of the body, driving force and surface charge that provide conditions conducive to ectopic bone formation.

A biomaterial is a material that is suitable for use in vivo. A biomaterial can be described as being biocompatible, meaning that, according to ISO 10993, the material performs, replaces or augments biological function. The biomaterial may be a replacement bone material. For example, it may be used as a synthetic bone material, including dental materials, for example for use in bone substitution, implants, fillers and cements, coatings for metallic implants and for making hydroxyapatite-polymer composites.

Looking at each of the factors in greater detail that in combination beneficially result in osteoinductive behaviour, the inventors have found that, in order to promote the absorption of bone growth-promoting factors from biological fluids onto the surface of the biomaterial, the surface free energy of the biomaterial of the present invention is 19 mJ/m$^2$ or greater.

The surface free energy, mJ/m$^2$, is measured using Kruss Drop Analysis of contact angles for liquids with a known liquid-vapour interfacial free energy on fully-dense surfaces of the same material chemistry.

Preferably, the surface free energy is 20 mJ/m$^2$ or greater, for example 30 mJ/m$^2$ or greater, such as 35 mJ/m$^2$ or greater, for example 40 mJ/m$^2$ or greater, such as 50 mJ/m$^2$. Preferably, the maximum free energy is 57 mJ/m$^2$, for example 50 mJ/m$^2$, such as 45 mJ/m$^2$. Thus, illustrative ranges of preferred surface free energy are 30 to 57 mJ/m$^2$ such as 40 to 57 mJ/m$^2$; more preferably from 35 to 50 mJ/m$^2$; even more preferably from 35 to 45 mJ/m$^2$. While the inventors have found osteoinductive behaviour to increase with surface free energy, the inventors have found that the surface properties of the biomaterial can change if the surface free energy approaches 57 mJ/m$^2$.

The surface free energy of a substrate may be controlled by techniques known in the art, for example, varying chemical composition, nanoscale texture, doping, substitutions, contamination, or subjecting the material to heat or chemical treatments. For example, the inventors have found that the surface free energy and osteoinductive behaviour is increased in a calcium phosphate material when silicon (e.g. as a silicate ion) is added to the material.

The inventors have also found that a porous biomaterial having a specific pore structure in combination with the surface free energy described herein has the potential to promote bone formation on or around the surface of the material when implanted at a non-bony site. Specifically, the porous biomaterial of the present invention comprises a network of interconnected micropores. The inventors have found that a beneficial increase in osteoinductive behaviour occurs at a microporosity of at least 17.5% by volume, more beneficially 23% by volume. Below these values, the inventors have found less osteoinduction to occur.

As used herein, the term "micropores" are those pores measured by mercury intrusion porosimetry analysis to have an interconnection diameter of 50 nm to 10 μm. While only some of the interconnections between neighbouring will be circular, the term interconnection diameter refers to the equivalent circular diameter of the pores as measured by mercury intrusion porosimetry. The term "microporosity" refers to the porosity resulting from micropores.

Porosity of the biomaterial is measured by mercury intrusion porosimetry analysis. In particular, the following conditions may be used for this measurement: an advancing contact angle of 140 degrees, a liquid-vapour interfacial free energy for mercury of 0.480 mJ/m$^2$, and a mercury density of 13.5335 g/ml. The measurement may be carried out at ambient temperature and pressure (20° C. and 1 atmosphere). The total pore volume within a range of interconnection diameters may be measured by mercury intrusion porosimetry volume fraction measurement of pores.

Preferably, the microporosity is 19% by volume or more, such as 20% by volume or more. Beneficially, the microporosity is 23% by volume or more, such as 24% by volume or more, for example 25% by volume or more, such as 30% by volume or more, for example 35% by volume or more. The microporosity may be 60% by volume or less, for example 55% by volume or less or 50% by volume or less, such as 40% by volume or less, for example 35% by volume or less, such as 30% by volume or less. In an illustrative example, the microporosity may be preferably 23 to 60% by volume, for example 23% to 50% by volume or 30% to 50% by volume, such as 23% to 40% by volume, for example 25 to 35% by volume, for example about 26% by volume. In particular, the inventors have surprisingly found osteoinduction to increase with the microporosity. This may be because wicking capacity is observed also to increase with microporosity. However, the inventors have found that a maximum level of microporosity is preferable so that pores do not coalesce, thereby possibly reducing the capillary pressure of the biomaterial.

If the biomaterial contains pores other than the micropores as discussed later (e.g macropores), the microporosity satisfies the following relationship:

$$V_m \geq 0.175(V_T - V_O)$$

where $V_T$ is the total volume of the biomaterial, $V_s$ is the total volume of the micropores and $V_O$ is the total volume of the pores other than the micropores. If there is no other porosity than the microporosity, then $V_O = 0$.

Preferably, at least 90% by number of the pores having an interconnect diameter of less than 10 μm have an interconnect diameter of 50 nm to 10 μm; more preferably, at least 90% by number of the pores having an interconnect diameter of less than 10 μm have an interconnect diameter of 0.1 to 8 μm; still more preferably, at least 90% by number of the micropores having an interconnect diameter of less than 10 μm have an interconnect diameter of 0.1 to 5 μm. Working within these ranges is thought to increase the osteoinductive properties of the biomaterial. Thus, while the porous body may have some pores having an interconnection diameter less than that of the micropores, these pores are not thought to contribute to the osteoinductive properties of the porous body. Therefore, preferably the body does not contain a significant number of pores (i.e. substantially no pores) having an interconnection diameter of less than 50 nm. Preferably, these numbers of pores having these specific ranges of interconnect diameter are 95% by number, more preferably 98% by number, and more preferably 99% by number.

The microporosity preferably comprises an open porous network. This is thought to favour a high permeability and wicking capacity. Thus, the micropores may have an interconnect level of 90% or greater, more preferably 96% or greater, and even more preferably 99% or greater. The interconnection level (vol/vol %) is measured by Helium Pyconometry measurement and a theoretical density for the same material.

The mean interconnect diameter of the micropores is chosen so to provide the porous body with a permeability and capillary pressure difference that allow biological fluids and proteins to penetrate the body effectively. In particular, while the inventors have found that a low mean interconnection diameter contributes to a beneficial capillary pressure difference, it may also contribute to a low permeability. Accordingly, the mean interconnect diameter of the micropores may be 0.5 μm or more, for example 0.7 μm or more.

The minimum mean interconnect diameter may beneficially preferably be chosen to provide a minimum permeability of 0.206 nm$^2$, and more preferably the preferred minimum permeability values described herein. Using the relationship between permeability and the mean interconnect diameter described herein, this is the equivalent of a minimum mean interconnect diameter of about 0.8 μm.

The interconnection diameter of the pores is measured by mercury intrusion porosimetry analysis. In particular, the following conditions are used for this measurement: an advancing contact angle of 140 degrees, a liquid-vapour interfacial free energy for mercury of 0.480 mJ/m$^2$, and a mercury density of 13.5335 g/ml. The mean interconnection diameter is measured by obtaining a plot of pore size distribution (i.e. of pores size vs. number of pores having this pore size) using mercury intrusion porosimetry and then calculating the mean of the results by adding up the results and dividing by the integrated area of the plot.

More preferably, the minimum mean interconnect diameter is 0.813 μm, for example 0.9 μm, or 0.94 μm or more, such as 1.0 μm, for example 1.1 μm, or 1.25 μm or more, such as 1.3 μm or more.

The inventors have also found that, while a large mean interconnection size contributes to a beneficial permeability of the porous body, it may also contribute to a low capillary pressure difference. Accordingly, the mean interconnection diameter may preferably be 2.0 μm or less, such as 1.8 μm or less, for example 1.7 μm or less, such as 1.6 μm or less, for example 1.5 μm or less, for example 1.4 μm or less.

The maximum mean interconnect diameter may beneficially preferably be chosen to provide a minimum capillary pressure difference in water of 3.7 kPa, and more preferably the preferred capillary pressure difference values described herein. Since capillary pressure difference depends both on surface free energy and mean interconnection diameter, the maximum mean interconnection diameter for any material depends on the material's surface free energy in order to satisfy this preferable condition.

To take illustrative examples of preferred ranges of the mean interconnection diameter, the mean interconnection diameter of the pores may preferably be 0.5 μm to 2.0 μm, for example 0.75 μm to 1.8 μm, for example, 0.813 μm to 1.7 μm, such as 1.0 to 1.5 μm, for example 1.3 μm to 1.4 μm, such as about 1.3 μm. As described above, the inventors have found the lower upper limits of mean interconnection diameter can result in an advantageous permeability to allow biological fluid to flow through the biomaterial, but that a larger mean interconnection diameter can contribute to a low capillary pressure. The inventors have also found the upper lower limits of mean interconnection diameter can result in an advantageous capillary pressure difference to increase the driving force of the up-take of biological fluids into the biomaterial, but that a lower mean interconnection diameter can contribute to a low permeability. Accordingly, the minimum and maximum mean interconnection diameters may be chosen to provide the preferred permeability resulting from the micropores and the preferred capillary pressure difference in water described herein, for example a permeability of 0.206 m$^2$ or greater and a capillary pressure difference of 3.7 kPa or more.

Going into greater detail about the permeability and the capillary pressure difference resulting from the value of the mean interconnection size, the inventors have found that, in order to allow a level of wicking of biological or circulatory fluid into the micropores which beneficially supports osteoinductivity, the biomaterial preferably has a permeability through the small-scale interconnected porosity (i.e. resulting from the micropores) of 0.206 nm² or greater. As described above, the permeability can be controlled by varying the distribution of the interconnection diameters of the pores and this minimum preferred permeability may be achieved by selecting a preferred minimum mean interconnection size of about 0.8 μm.

The permeability is determined from the results of the mercury intrusion porosimetry as follows:

$$K = \frac{\Phi d_p^2}{32}$$

where K is the permeability resulting from the micropores (small pores); and $d_p$ is the mean interconnect diameter of the micropore interconnections as calculated from the mercury intrusion porosimetry measurement of the interconnect size. $\Phi$ is the volume fraction of pores filled with mercury.

Preferably, the permeability is 0.8 nm² or more; more preferably, it is 1.0 nm² or more. The permeability may be 10 nm² or less, such as 5 nm² or less, for example 3 nm² or less. For example, in one embodiment, the permeability may be 0.8 nm² to 5 nm². The inventors have found bone growth to be beneficially achieved within these limits.

Regarding the capillary pressure difference, the maximum mean interconnection diameter of the micropores may be chosen to provide the porous body with a minimum capillary pressure difference in water of 3.7 kPa. Using the relationship between capillary pressure difference and the mean interconnect diameter described herein, this is the equivalent of a maximum mean interconnect diameter (r) satisfying the relationship:

$$r = \frac{2\gamma_{LV} \cos(\Theta)}{\Delta P_{MINIMUM}}$$

where $\Delta P_{MINIMUM}$ is the appropriate minimum Capillary Pressure Difference, $\gamma_{LV}$ (mJ/m²) is the liquid-vapour interfacial free energy of the liquid in contact with the same material, θ is the contact angle of the liquid on the same material, and r (in m) is the mean interconnection diameter of the micropores measured by mercury porosimetry. Thus, the maximum mean interconnection size is dependent on the surface free energy.

Accordingly, the inventors have found that, in order to encourage the absorption of bone growth-promoting factors from biological fluids into the biomaterial, the capillary pressure difference of the material is advantageously above 3.7 kPa when measured in water. As described above, the capillary pressure difference can be controlled by varying the surface free energy of the biomaterial and the distribution of micropores within the material (in particular, the distribution of the interconnect diameters of the pores).

The Capillary Pressure Difference is measured in water and determined from the following relationship between the surface free energy and the interconnection diameter:

$$\Delta P = 2\gamma_{LV} \cos(\partial)/r$$

where $\Delta P$ is the Capillary Pressure Difference, $\gamma_{LV}$ (mJ/m²) is the liquid-vapour interfacial free energy of the liquid in contact with the same material, θ is the contact angle of the liquid on the same material, and r (in m) is the mean interconnection diameter of the micropores measured by mercury porosimetry.

In this equation, the liquid-vapour interfacial free energy can be determined by the Young's equation, which describes the energies at the boundary between liquid, vapour and solid when a drop of liquid (e.g. water) forms on the surface of material:

$$\gamma_{SV} = \gamma_{LV} \cos \partial + \gamma_{SL}$$

Here, $\gamma_{SV}$ is the solid-vapour interfacial energy (measured in mJ/m²), θ is the contact angle and $\lambda_{SL}$ is the solid-liquid interfacial energy. All interfacial measurements are made using the Kruss drop analysis technique described herein.

Preferably, the capillary pressure difference is 3.9 kPa or above such as 3.97 kPa or above, such as 15 kPa or greater, for example 25 kPa or above, or 36 kPa or above, such as 40 kPa or above, more preferably, it is 50 kPa or above. The capillary pressure difference may be 150 kPa or less, such as 100 kPa or less, for example 85 kPa or less, such as 70 kPa or less. Thus, in one illustrative example, the capillary pressure difference of the biomaterial is preferably 3.7 kPa to 100 kPa, such as 20 kPa to 100 kPa. The inventors have found bone growth to be beneficially achieved within these limits.

By providing a porous body with the porosity and distribution of mean interconnection diameters according to the invention, the inventors have found that the porous body may provide a permeability and a capillary pressure difference that allow biological fluids and proteins to penetrate the body effectively. The interconnection size of the micropores is limited to 10 μm or less so that sufficient capillary pressure difference is provided by these pores. Since the inventors have found the intrinsic osteoinductive behaviour of the biomaterial to depend on the permeability of the material due to its micropores and the capillary pressure difference of the material, the up-take of biological fluids and proteins by the body resulting from the micropore structure directly contributes to the osteoinductive properties of the biomaterial.

Preferably, in order to allow the rapid transport of circulatory and biological fluids within the biomaterial and allow advantageous build-up of bone growth-promoting materials absorbed from a biological medium, the biomaterial preferably has a total wicking capacity (vol/vol %) of 400% by volume or more. (Both the micropores and optional macropores contribute to the total wicking capacity). The total wicking capacity may be controlled by varying the total pore volume of the biomaterial (both micro- and macro-pores) and the interconnection level of the pores in the biomaterial.

The total wicking capacity (vol/vol %) of a single material over the entire pore size range is derived from an Archimedes density measurement using water. Water is used rather than a biological medium such as blood in order to increase the reproducibility of the measurement.

Preferably, the total wicking capacity is 420% by weight or greater; more preferably, it is 430% by weight or greater. The wicking capacity may be 800% by weight or less, such as 600% by weight or less, for example 500% by weight or less. In one illustrative example, the total wicking capacity may be preferably 400% to 600%, for example 420 to 500%. The inventors have found bone growth to be beneficially achieved within these limits.

Preferably, the total wicking capacity attributed to the micropores may be maximized. The wicking capacity of the micropores is affected by the permeability of the micropores and the capillary pressure difference. However, in order to maintain the structural benefits of the scaffold, an upper limit may be placed on the wicking capacity.

Preferably, the porous body may also have a number of pores with a large interconnect diameter connecting one pore to the next so as to allow the rapid and complete transport of circulatory and biological fluids within the biomaterial. Therefore, in addition to the micropores, the biomaterial of the present invention may comprise macropores. As used herein, the term "macropores" refers to pores having a mean interconnection diameter of more than 10 µm. While not required, this network of large pores (macropores) is thought to facilitate the transport of circulatory and biological fluids within the biomaterial. This can increase the rate at which biological fluids and proteins are absorbed into the micropores (micropores) and adsorbed onto the surfaces of the biomaterial. Preferably, at least 90% of the macropores (more preferably, 95%, even more preferably 98%) of the macropores have an interconnect diameter of 50 µm or more.

Preferably, the macroporosity (i.e. the porosity resulting from the macropores) is 20% by volume or greater, for example 30% or greater, such as 40% or greater. The macroporosity may be 70% or less, for example 60% or less, such as 50% or less. In one exemplary embodiment, the macroporosity is preferably 20% to 60% by volume. Within these limits, the beneficial effect of circulating biological fluids and proteins to the micropores may be increased.

While the porous body may have some pores having an interconnection diameter less than that of the micropores, these pores are not thought to contribute to the osteoinductive properties of the porous body. Therefore, preferably the body does not contain a significant number of pores (i.e. substantially no pores) having an interconnection diameter of less than 50 nm.

Preferably, if the body contains both macropores and micropores, the overall porosity of the body of the present invention is preferably, as measured by archimedes density measurement using water, 45% by volume or greater, such as 50% by volume or greater, for example 60% by volume or greater, such as 70% by volume or greater. The inventors have found that these lower limits can contribute to a beneficial osteoinductive effect. Preferably, the overall porosity is 95% by volume or less, such as 90% by volume or less, for example 85% by volume or less. The inventors have found that, above these upper limits, coalescence of pores may occur resulting in reduced benefit from osteoinduction. Thus, an illustrative example of a preferred range of overall porosity is 50% to 90% by volume.

Turning to the chemical make-up of the biomaterial of the present invention, in its broadest aspect, the biomaterial of the present invention is not limited by its chemical composition. For example, it may be organic or inorganic, or may contain both organic and inorganic species. For example the biomaterial may be, for example, a ceramic or a polymer.

Whatever the chemical composition of the biomaterial, the biomaterial is preferably non-resorbable. The term non-resorbable refers to a chemically stable biomaterial. The term is defined to refer to a non-soluble material. Specifically, the material may show no significant structural dissolution when it is immersed in water. Since resorption may be dependent on porosity, in order to compare the resorption of different materials, the level of resorption is measured for the bulk material and on samples having the same surface area.

The inventors have recognised that the resorption of the scaffold into the body can occur in part or in whole prior to effective bone formation. Furthermore, the inventors have found that the total dissolution products of a scaffold can potentially impede or reduce the rate of bone formation as the local biochemical environment becomes saturated with high concentrations of foreign ionic species. The inventors have also found that these drawbacks to resorbable materials can result in low and inconsistent levels of bone formation. This inconsistency has also made in vivo validation of the principle of using a material with intrinsic osteoinductive properties difficult.

Accordingly, the present invention preferably provides a chemically stable (non-resorbable) scaffold for bone material which reliably and reproducibly induces significant levels of bone formation when tested in ectopic sites in preclinical models. Such bone formation is intimately associated with the scaffold itself, rather than being associated with either cytokines or dissolution products provided or associated with the scaffold. This ensures that accelerated bone formation occurs only where the scaffold is implanted, rather than at random wherever circulatory fluids transport adsorbed cytokines or dissolution products.

Thus, preferably the material contains 90% or more of non-resorbable phases (as measured by X-ray diffraction), preferably 95% or more, more preferably 98% or more, such as 99% or more, for example about 100%. In other words, preferably all of the material is non-resorbable, disregarding inevitable impurities.

In one embodiment, the biomaterial is a porous ceramic, such as a calcium phosphate material. An example of a non-resorbable calcium-phosphate material is hydroxyapatite.

If the biomaterial is a calcium phosphate material, one preferred method of modifying the surface free energy of a calcium phosphate material is to add silicon to the calcium phosphate material to provide a silicon-containing calcium phosphate material. Preferably, silicon is preferably contained in the calcium phosphate material in an amount of 0.1 to 5.0 weight %. More preferably, it is contained in an amount of 0.5 to 1.6 weight %, such as 0.5 to 1.0 weight %, for example about 0.8 weight %. The silicon may, for example, be substituted into the crystal lattice to render it less resorbable. As such, the silicon may exist in the form of, for example, a silicon ion or a silicate ion. The inventors have found that these ranges of silicon content results in enhanced osteoinduction.

A suitable method of forming a silicon-substituted hydroxyapatite material in which silicon is substituted into the crystal lattice and which has substantially no impurity phases of calcium oxide and/or tricalcium phosphate, and having a phase purity, as measured by X-ray diffraction, of at least 98%, is described in EP 0951441, the contents of which are incorporated herein by reference.

The biomaterial may itself be a replacement bone material, i.e. it may comprise a scaffold, for example a scaffold based on a calcium phosphate (e.g. hydroxyapatite).

Whatever the chemical composition of the biomaterial, the biomaterial may be used, for example, to treat bone fractures, achieve spinal fusions or to repair bone tumors or vertebral compression fractures. In these uses, the biomaterial is implanted into a patient or animal. This may be achieved using techniques known in the art. The present invention also provides for a synthetic bone material, bone implant, orthopaedic implant, tissue implant, bone graft, bone substitute, bone scaffold, filler, coating or cement comprising a composition as herein described. The present invention also provides for the use of the compositions as herein described in these applications. The present invention also provides for a method of treating a patient, the method comprising delivering a bioceramic composition as herein described to a site in the patient to be treated. The present invention also provides a bioceramic composition as herein described for use as a biomedical implant. The present invention also provides a bioceramic composition as herein described for use in therapy. The present invention also provides a bioceramic composition as herein described for use in reconstructive or replacement surgery.

It will be appreciated that bioceramic composition as herein described may be used in these biomedical applications on its own or in conjunction with one or more of a biocompatible polymer, other type of ceramic, glass, and/or glass-ceramic material.

The biomaterial may be provided in any known form, for example as dry granules, as a paste with a solvent (e.g. water or blood), in a binder or as a solid pre-formed, preshaped implant.

The present invention further provides a method of selecting a porous osteoinductive biomaterial and providing osteoinduction of the bone, the method comprising: (a) selecting an osteoinductive porous biomaterial having the following characteristics: (i) a network of interconnected micropores having a microporosity set to 17.5% by volume or more, (ii) a surface free energy set to 19 mJ/m$^2$ or more, (iii) a permeability resulting from the micropores set at 0.206 nm$^2$ or greater, and (iv) a capillary pressure difference in water set to 3.7 kPa or more; and (b) configuring said osteoinductive biomaterial as a replacement bone-material for osteoinduction. More beneficially, the microporosity may be set at 23% by volume or more.

The present invention further provides the use of a microporosity of 17.5% by volume or more, a surface free energy of 19 mJ/m$^2$ or more, a permeability resulting from the micropores of 0.206 nm$^2$ or greater and a capillary pressure difference in water of 3.7 kPa or more to impart osteoinductive properties to a synthetic porous biomaterial. Osteinductive properties refer to the inherent ability of a biomaterial to exhibit osteoinduction. More beneficially, the microporosity may be set at 23% by volume or more.

All measurements of the physical properties described herein are made at room temperature (20° C.) and atmospheric pressure (1 atmosphere) unless stated otherwise.

EXAMPLES

Several samples were prepared from material synthesised according to the method described in EP 0951441. The material was then processed into a porous biomaterial according to the present invention using the foaming method described in WO0020353. The entire contents of WO0020353 are incorporated herein by reference. Using this technique, pore size and porosity was controlled to achieve the desired pore sizes and porosities by varying the relative proportions of the ingredients within the ceramic slip, the physical characteristics of the ceramic particulate, the amount of milling media added during mill-foaming and, additionally by the sintering procedure.

These samples were then implanted in an animal and their osteoinductivity was measured. Results are shown in Table 1. To measure the osteoinductivity of the samples, the calcium phosphate biomaterials were implanted into the right and left sacrospinalis muscle of skeletally mature female commercially cross bred sheep aging greater than two years and weighing between 65 and 80 kg. Animals were euthanized at week 12. After sacrifice, implants surrounded by a layer of muscle were removed and fixed for histology. Radiography was carried out to locate the implants in the muscle. Thin sections of ~70 μm thick were prepared by ultramicrotomy in a proximal distal direction. Image analysis and histomorphometry was carried out on thin sections to assess bone formation within the implants. Percentage of bone area, soft tissue area and the area occupied by the test material were calculated. In addition percentage of the amount of bone attached to the calcium phosphate surfaces was measured. Scanning Electron Microscopy (SEM) and EDAX were also carried out to evaluate the quality of bone formation and the elements present within the implants.

| Ex. | Material | Surface free energy (mJ/m$^2$) | Micro-porosity (% Vol) | Mean inter-connection diameter (μm) | Capillary pressure difference (kPa) | Permeability (nm$^2$) | Bone Area (%) |
|---|---|---|---|---|---|---|---|
| 1 | SiHA | 38.31 | 0.9 | 1.743 | 37.8 | 2.161 | 0.00 |
| 2 | SiHA | 38.31 | 4.1 | 0.9436 | 69.8 | 0.206 | 0.00 |
| 3 | SiHA | 38.31 | 18.2 | 1.817 | 36.2 | 2.419 | 1.96 |
| 4 | SiHA | 38.31 | 20.0 | 0.7989 | 82.4 | 0.075 | 2.15 |
| 5 | SiHA | 38.31 | 26.4 | 1.347 | 48.9 | 1.158 | 8.26 |
| C1 | HA | 19.49 | 19.7 | 1.075 | 4.7 | 0.586 | 0.54 |
| C2 | HA | 19.49 | 16.8 | 0.9844 | 5.2 | 0.883 | 0.57 |
| C3 | HA | 19.49 | 21.3 | 1.368 | 3.7 | 1.343 | 0.86 |

SiHA = silicon-substituted hydroxyapatite (0.8 weight % with silicon).
HA = hydroxyapatite.

The invention claimed is:

1. A synthetic osteoinductive porous silicon containing calcium phosphate biomaterial comprising a network of interconnected micropores, wherein the microporosity is 23% by volume or more and has a surface free energy of 19 mJ/m$^2$ or more, wherein the mean interconnection diameter and the surface free energy are chosen to provide a permeability resulting from the micropores of 0.206 nm$^2$ or greater and a capillary pressure difference in water of 3.7 kPa or more.

2. The biomaterial according to claim 1, wherein the micropores resulting in the microporosity of the biomaterial have an interconnection diameter in the range of 50 nm to 10 μm.

3. The biomaterial according to claim 1, wherein the minimum mean interconnection diameter of the biomaterial is 0.9 μm.

4. The biomaterial according to claim 1, wherein the maximum mean interconnection diameter of the biomaterial is 2.0 μm.

5. The biomaterial according to claim 1, wherein the total wicking capacity (vol/vol %) of the biomaterial is 400% by volume or more.

6. The biomaterial according to claim 1, wherein the biomaterial is non-resorbable.

7. The biomaterial according to claim 1, wherein the synthetic osteoinductive porous biomaterial composition comprises dry granules.

8. The biomaterial according to claim 1, wherein the synthetic osteoinductive porous biomaterial composition comprises a paste.

9. The biomaterial according to claim 1, wherein the synthetic osteoinductive porous biomaterial composition comprises a binder.

10. The biomaterial according to claim 1, wherein the synthetic osteoinductive porous biomaterial composition comprises a solid preformed, preshaped implant.

* * * * *